United States Patent [19]

Bhatt

[11] Patent Number: 5,252,723
[45] Date of Patent: Oct. 12, 1993

[54] METHOD AND REAGENT FOR SULFURIZATION OF ORGANOPHOSPHOROUS COMPOUNDS

[75] Inventor: Ram S. Bhatt, San Diego, Calif.

[73] Assignee: Gen-Probe, Inc., San Diego, Calif.

[21] Appl. No.: 618,629

[22] Filed: Nov. 27, 1990

Related U.S. Application Data

[62] Division of Ser. No. 319,570, Mar. 6, 1989.

[51] Int. Cl.$^5$ .............................................. C07H 1/00
[52] U.S. Cl. ................................ 536/25.3; 536/25.34; 536/124; 536/126
[58] Field of Search ............... 536/27, 29, 25.3, 25.34, 536/29.13, 124, 126

[56] References Cited

U.S. PATENT DOCUMENTS

| | | | |
|---|---|---|---|
| 2,536,647 | 1/1951 | Kosolapoff | 260/461 |
| 2,647,140 | 7/1953 | Jonas | 260/461 |
| 2,907,787 | 10/1959 | Hoffman et al. | 260/461 |
| 3,162,570 | 12/1964 | Wilson | 167/22 |
| 3,294,874 | 12/1966 | Schrader | 260/948 |
| 3,296,221 | 1/1967 | Stanley | 260/79 |
| 3,687,808 | 8/1972 | Merigan et al. | 195/28 |
| 4,189,453 | 2/1980 | Zinke et al. | 260/976 |
| 4,625,677 | 12/1986 | Neher | 118/713 |

FOREIGN PATENT DOCUMENTS

| | | | |
|---|---|---|---|
| 661668 | 4/1963 | Canada | 260/461 |
| 1346409 | 2/1974 | United Kingdom | 409/36 |

OTHER PUBLICATIONS

Hata, T. & Sekine, M. Oxidation of Nucleoside Phosphites By Means of 2,2'Dipyridyl Disulfide Via Nucleoside Silylphosphite Intermediates Tetrahedron Letters No. 45, pp. 3943-3946 (1974).

Chen, J. & Benkovic, S. Synthesis and Separation of Diastereomers of Deoxynucleoside 5' O-(1-Thio) Triphosphiates.

Nucleic Acids Research 11, 3737-3751 (Jun. 11, 1983).

Lamande, L., et al.-Synthesis of a Triethylammonium Salt of a Spirophosphorane Containing a P-SH Bond. Society of Chemical Communications 49, 2314-2317 (1984).

*Primary Examiner*—John W. Rollins
*Assistant Examiner*—James O. Wilson
*Attorney, Agent, or Firm*—Lyon & Lyon

[57] ABSTRACT

A composition suitable for sulfurizing an organophosphite. The reagent comprises a solution of sulfur and a non-aromatic tertiary amine, in a suitable solvent such as carbon disulfide. The non-aromatic tertiary amine is preferably an optionally substituted trialkyl amine, for example triethylamine or diisopropylethylamine. A method is also provided in which phosphites or phosphonates are sulfurized to their corresponding phosphorothioates or phosphonothioates, respectively, using compositions of the present invention. This method has particular application to produce internucleotide phosphorothioate or phosphonothioate bonds in a nucleotide multimer.

22 Claims, 2 Drawing Sheets

METHOD AND REAGENT FOR SULFURIZATION OF ORGANOPHOSPHOROUS COMPOUNDS

This application is a division of copending U.S. patent application Ser. No. 07/319,570, filed Mar. 6, 1989, pending.

FIELD OF THE INVENTION

This invention relates to the sulfurization of phosphites and phosphonites. In another aspect it relates to phosphorothioate analogs of nucleic acids. In another aspect it relates to methods for synthesizing such analogs. In a further aspect it relates to reagents useful in the sulfurization of phosphites and phosphonites, for example, the synthesis of phosphorothioate analogs of nucleic acids.

BACKGROUND OF THE INVENTION

Nucleic Acids occur in nature as chains of either ribonucleotides or deoxyribonucleotides, the individual nucleotides being linked to each other by phosphodiester bonds between the ribose and deoxyribose sugars which form, respectively, the backbones of ribonucleic nucleic acid (RNA) or deoxyribonucleic acid (DNA). Apart from their role in naturally occurring phenomena, DNA and RNA, particularly DNA and RNA oligonucleotides, are expected to play an increasingly important role in medical diagnostic and therapeutic applications. For example, oligonucleotides have been shown to be useful in a variety of "probe" assays for viral and bacterial diseases and for the detection of genetic abnormalities. In these assays, the "probe" is typically an oligonucleotide selected to complement an RNA or DNA sequence which is unique to the organism or genetic defect to be detected.

It has also been observed that oligonucleotides which are complementary to messenger RNA (antisense oligonucleotides) can be introduced to a cell and arrest the translation of the mRNA. This arrest is believed to result from the hybridization of the antisense oligonucleotide to the mRNA. See, for example, Stephenson, et al, *Proc. Natl. Acad. Sci.*, USA, 75, 285 (1978) and Zamecnik, et al., *Proc. Natl. Acad. Sci.*. USA, 75, 280 (1978).

The ability of antisense oligonucleotides to inhibit or prevent mRNA translation suggests their application in antiviral therapy. A virus infecting a cell reproduces its genetic information by using the biological machinery of the infected cell. Transcription and translation of that information by the cellular ribosomes are essential to viral reproduction. Thus, if expression of the viral gene can be interrupted, the virus cannot replicate or may replicate at such a slow rate as to give the host's immune system a better opportunity to combat the infection.

It has been proposed to use oligonucleotides in viral therapy by designing an oligonucleotide with a nucleotide sequence complementary to a sequence of virally expressed mRNA which must be translated if viral replication is to be successful. Introduction of the antisense oligonucleotide to the cell permits it to hybridize with and prevent, or at least inhibit, this essential translation.

Conventional phosphodiester antisense oligonucleotides have been reported to exhibit significant shortcomings as antisense oligonucleotides. One limitation is that they are highly subject to degradation by nucleases, enzymes which breakdown nucleic acids to permit recycling of the nucleotides. In addition, most cells are negatively charged. As a result, a phosphodiester oligonucleotide does not readily penetrate the cell membrane because of the density of negative charge in the backbone of the oligonucleotide.

It has been proposed to modify oligonucleotides to overcome these shortcomings. One such proposal has been to use non-polar analogs of conventional phosphodiester oligonucleotides. Such analogs retain the ability to hybridize with a complementary sequence and would be expected to enter the cell more readily and be less resistive to nuclease degradation. Promising results have been obtained with methyl phosphonate analogs. See Agris et al., *Biochemistry* 25, 1228 (1986). More recently thiophosphorate analogs, i.e., nucleic acids in which one of the non-bridging oxygen atoms in each inter-nucleotide linkage has been replaced by a sulfur atom, have also been shown to possess the ability to block mRNA translation. In at least one case, inhibition of expression of the chloramphenicol acetyltransferase gene, a thiophosphorate analog has been shown to be superior to the methyl phosphonate analog which in turn was shown to be more effective than the unmodified phosphodiester oligonucleotide. Inhibition of HIV virus replication by a thiophosphorate analog has also been demonstrated. See Matsukara et al, *Proc. Natl. Acad. Sci.*, USA, 84, 1 (1987).

Thiophosphorate analogs of oligonucleotide probes are also useful as replacements for conventional probes in diagnostic applications as described above, and in other applications of oligonucleotides. However, only a few techniques have been reported for the synthesis of phosphorothioate analogs of nucleic acids, all of them cumbersome and not well adapted for use with currently available automated nucleic acid synthesizers.

One reported synthetic technique, for example, uses presynthesized nucleotide dimers. The synthesis of the full array of sixteen dimers necessary for the procedure is both laborious and expensive.

A more preferred procedure would permit use of the highly reactive, commercially available nucleoside-phosphoramidite monomers currently employed with nucleic acid synthesizers. Such monomers are actually used in processes for preparing phosphorothioate analogs. However, the sulfurization of phosphorous in the phosphite intermediate has been very troublesome. For example, elemental sulfur in pyridine at room temperature requires up to 16 hours to produce internucleotide phosphorothioate triester 12. (P. S. Nelson, et al., *J. Org. Chem.*, 49, 2316 (1984); P. M. S. Burgers, et al., *Tet Lett.*, 40, 3835 (1978)). A similar procedure using elemental sulfur, pyridine and carbon disulfide permitted sulfurization to be done at room temperature within 2 hours. B. A. Connolly, et al., *Biochem.*, 23, 3483 (1984). The triester is convertible to the phosphorothioate by base catalyzed removal of substituent "R."

Carrying out the sulfurization at 60° C. in 2,6-lutidine requires 15 minutes during automated, solid-phase synthesis of phosphothioates from Compound 11. W. J. Stec et al., *J. Am. Chem. Soc.*, 106, 6077 (1984). However, most automated synthesizers do not have provisions for heating the column required for performing sulfurization at elevated temperature and vaporization of the solvent at 60° C. would be expected to form bubbles in delivery lines which would reduce flow rates and even cause synthesis failures. In addition, even a fifteen minute reaction time for sulfurization after the addition of each nucleotide makes the procedure far from optimal.

Accordingly, there has gone unmet a need for a process for the preparation of phosphothioate oligonucleotide analogs that is rapid and that lends itself to use on conventional nucleic acid synthesizers.

Terminology

The following terms are used in this disclosure and claims:

Nucleotide: Refers to a subunit of a nucleic acid consisting of a phosphate group, a 5 carbon sugar ring and nitrogen containing purine or pyrimidine ring. In RNA the 5 carbon sugar is ribose. In DNA, it is 2-deoxyribose. The term also includes analogs of such subunits (eg. a subunit having a phosphonate, phosphorothioate or phosphonothioate group rather than a phosphate group). When the phosphate or the like group is not present or not being referred to, the remainder of the subunit is generally referred to as a "nucleoside".

Nucleotide multimer: A chain of two or more nucleotides linked by phosphorodiester or phosphonodiester bonds, or analogs thereof.

Oliconucleotide: A nucleotide multimer generally about 10 to 125 nucleotides in length, but which may be greater than 125 nucleotides in length. They are usually obtained by synthesis from nucleotide monomers, but may also be obtained by enzymatic means.

Nucleotide multimer probe: A nucleotide multimer having a nucleotide sequence complementary with a target nucleotide sequence contained within a second nucleotide multimer, usually a polynucleotide. Usually the probe is selected to be perfectly complementary to the corresponding base in the target sequence. However, in some cases it may be adequate or even desirable that one or more nucleotides in the probe not be complementary to the corresponding base in the target sequence, or that various moieties of synthetic origin either replace a nucleotide within the probe or be inserted between bases of the probe. Typically, the probe is labeled when used for diagnostic purposes.

Oligonucleotide probe: A probe of synthetic or enzymatic origin usually having less than about 125 nucleotides, but which may contain in excess of 200 nucleotides.

Hybridization: The formation of a "hybrid", which is the complex formed between two nucleotide multimers by Watson-Crick base pairings between the complementary bases.

SUMMARY OF THE INVENTION

The present invention then provides a reagent which is suitable for the convenient and efficient sulfurization of organic phosphites (i.e. trivalent phosphorus bonded to three oxy groups with at least one thereof being an organic-oxy group) and organic phosphonites (i.e. trivalent phosphorous bonded to only two oxy groups), to form the corresponding thiophosphorus acid derivatives (specifically, phosphorothioates or phosphonothioates, respectively). The invention is particularly suited to sulfurizing a suitably protected inter-nucleotide, either 3'-5' or 2'-5' phosphite or phosphonite linkages contained in oligonucleotides and ribonucleotide multimers in solution or on a solid support for the manual or automated synthesis of phosphothioate oligonucleotides.

Figure 1:
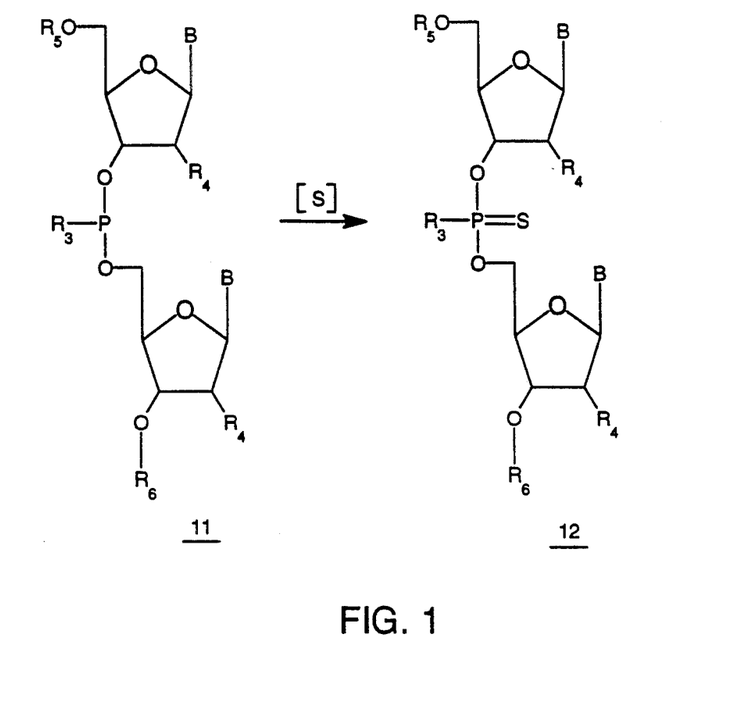
FIG. 1 shows the sulfurization of an oligonucleotide phosphite or phosphonite to form a phosphorothioate triester, or phosphonothioate diester, of a nucleic

Accordingly, the present invention provides, in one aspect, a reagent and process using that reagent suitable for adding "sulfur" to a phosphite or phosphonite intermediate of the kind 11 (see FIG. 1) to produce a phosorothioate or phosphonothioate of the kind (see FIG. 1). It should be noted that for compounds 11 the inter-nucleotide phosphite or phosphonite bond (and the inter-nucleotide phosphorothioate or phosphonothioate bond of 12) is shown between the 3'-hydroxyl of one nucleotide and the 5'-hydroxyl group of another nucleotide. However, those bonds can be between any two hydroxyl groups of two nucleotides, for example, between the 2' and 5' hydroxyls, or between the hydroxyl group of a nucleotide and that of a non-nucleotide moiety or even between two non-nucleotide moieties. The reagent comprises a mixture of elemental sulfur, a solvent for sulfur, and a tertiary alkyl amine. The preferred reagent is:

0.2 M elemental sulfur in a mixture comprising 50% carbon disulfide and 50% diisopropylethylamine.

Figure 3:
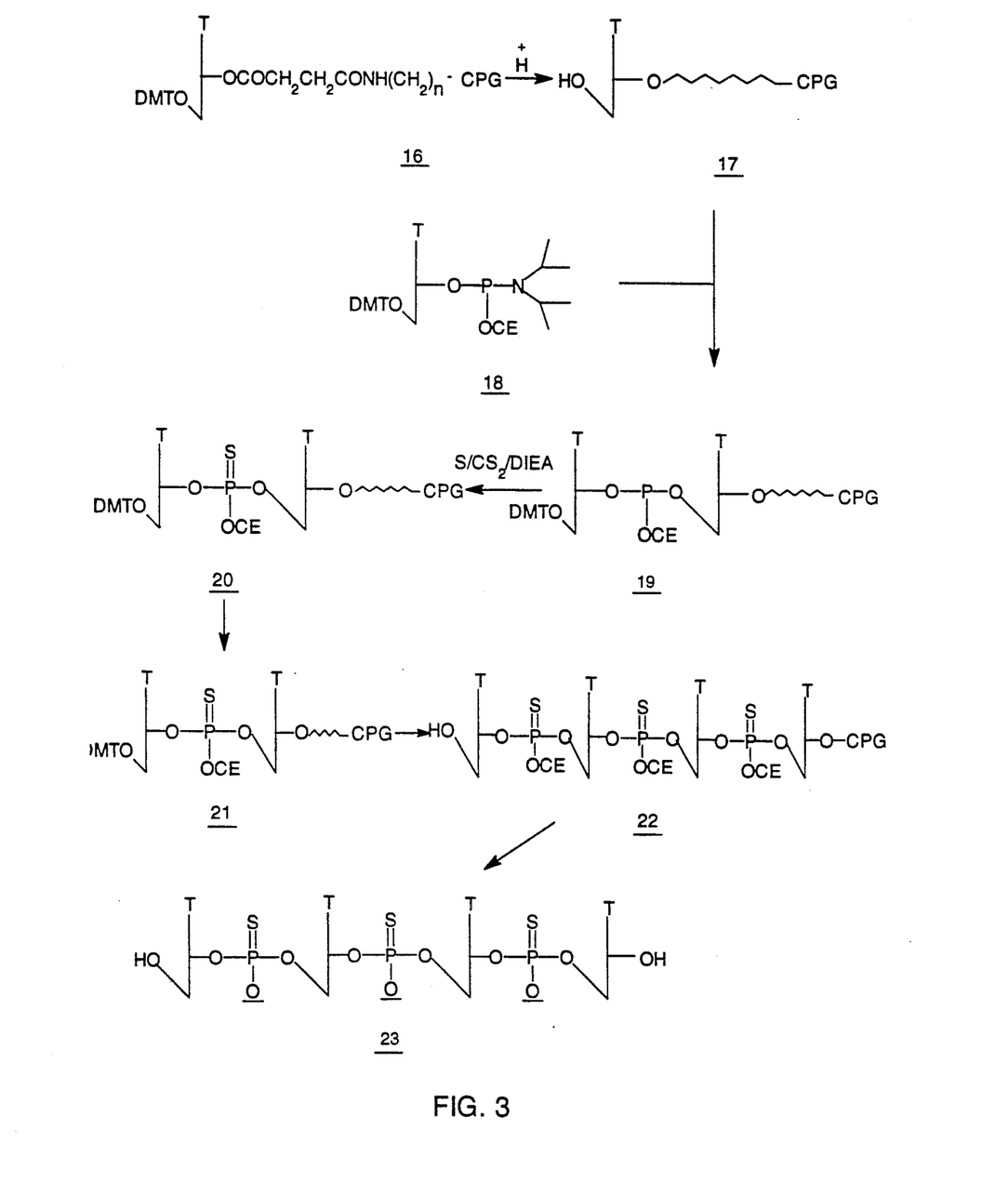
FIG. 3 illustrates assembly of an oligonucleotide phosphorothioate, involving sulfurization of oligonucleotide phosphites using a reagent of the present invention and its conversion to the corresponding phosphorothioate.

Other reagents of the present invention include:
(i) 0.2 M elemental sulfur in a mixture comprising 50% carbon disulfide and 50% triethylamine;
(ii) 0.2 M elemental sulfur in a mixture comprising carbon disulfide (25%), pyridine (25%) and triethylamine (50%). The above reagents can rapidly sulfurize the phosphite or phosphonite intermediates of the kind 15 at room temperature in just about 45 seconds, eliminating the need to choose between extended reaction times required for the sulfurization step if it is to be done at room temperature, or the use of elevated temperatures to achieve more rapid sulfurization as required by prior art processes. FIG. 3 illustrates a sulfurization process according to the invention as embodied in the synthesis of phosphorothioate analogs of oligonucleotides.

DESCRIPTION OF THE PREFERRED EMBODIMENTS

As described above, the reagent of the present invention comprises a mixture of elemental sulfur, an organic solvent for sulfur, and a non-aromatic tertiary amine. By a "non-aromatic" amine is meant an amine which is not a member of an aromatic ring (for example, pyridine is not a "non-aromatic" amine). However this term does not exclude an aromatic group bonded to the nitrogen of an amine group. The solvent for sulfur can be selected from solvents such as carbon disulfide, toluene, benzene or ethyl alcohol. Carbon disulfide is preferred as it is a particularly effective solvent for sulfur. The mixture can optionally include other substances, for example aromatic amines, such as pyridine. The useful tertiary amines include, for example, triethylamine and diisopropylethylamine. Diisopropylethylamine is preferred.

The composition of the reagent can vary over a wide range and the particular formulation which yields the best results can depend upon the phosphite or phosphonite being sulfurized. However, the most effective formulation of the reagent for a specific reaction can be determined by varying the components of the mixture. In addition, particular formulations may be found practically difficult to work with. For example, it was found that in a formulation in which 1,8-diazabicyclo[5,4,0]undec-7-ene was used as the tertiary amine, sulfur precipitated out from the carbon disulfide solution.

The reagents of the present invention, then, are useful for the sulfurization of organic phosphites or phosphonites to form the corresponding thioester. The starting organophosphorus compound, and its corresponding thioester produced by the method of the present invention, have the formulae:

phosphite or phosphonite phosphorothioate triester or phosphonothioate diester

In the above formulae, $R_1$, $R_2$, and $R_3$ may be the same or different and are selected from organic moieties such as optionally substituted alkyl, alkoxy, phenyl, phenoxy, and tertiary amino, and analogues of the foregoing. In particular, $R_1$ and $R_2$ are preferably ribonucleosides or deoxyribonucleosides.

The reagents of the present invention are particularly useful in the synthesis of phosphorothioate or phosphonothioate analogs of oligonucleotides from a phosphite or phosphonite in which $R_1$ and $R_2$ are nucleosides, particularly suitably protected nucleosides. In the case where it is desired to synthesize simply a phosphorothioate analog of a nucleotide multimer, then $R_3$ is a group which can be selectively removed (cleaved) following sulfurization. Examples of such groups include methoxy, and β-cyanoethoxy. However, if it is desired to produce a phosphonothioate analog of a nucleotide multimer (i.e., an analog in which a phosphonate linking group has an O= replaced with S=), then $R_3$ need not be a group which can be selectively removed following sulfurization. For example, $R_3$ could be methyl. Phosphites and phosphonites of the foregoing type are readily obtained using the processes of U.S. Pat. No. 4,725,677 and U.S. Pat. No. 4,458,066 (the disclosures of these patents, and all other references cited herein, being incorporated into this application by reference).

Figure 2:
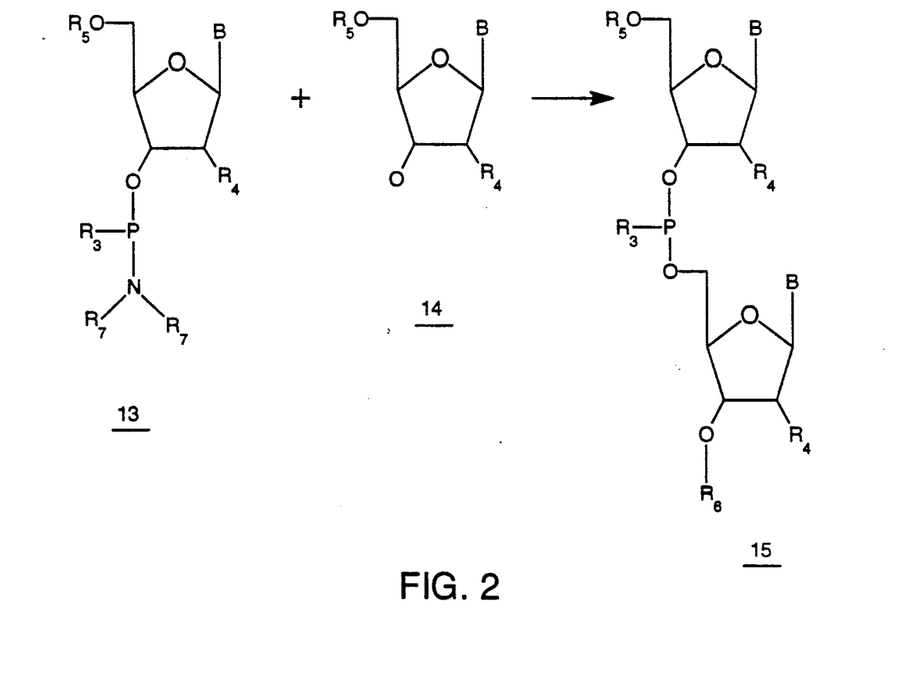
FIG. 2 illustrates the formation of an oligonucleotide phosphite triester or phosphonite diester useful in the invention.

FIG. 1 illustrates generally the sulfurization of internucleotide phosphite or phosphonite groups of a nucleotide multimer 11 to produce a nucleotide multimer 12 with internucleotide phosphorthioate or phosphonothioate groups, respectively, which results from using compositions of the present invention. FIG. 2 illustrates the assembly of a dinucleotide phosphite or phosphonite 15 from compounds of the type 13 (phosphoramidites or phosphonamidites) and 14 (nucleotides), using known procedures. However, it will be appreciated that higher oligomers can be obtained by sequential additions of phosphoramidites according to known procedures. Note that in FIGS. 1 and 2, the nucleosides are illustrated with some typical substituents, although other substituents might be present instead or in addition to those illustrated.

Sulfurization is preferably carried out after the addition of each nucleotide although sulfurization may be deferred and carried out on the assembled oligomer. The current reagent for the sulfurization of phosphites or phosphonites, particularly the internucleotides obtained from the phosphoramidite process, is 0.2 M elemental sulfur dissolved in an equal volume mixture of carbon disulfide and diisopropylethylamine.

Examples 1 and 2 below describe in detail the use of a sulfurizing reagent of the present invention for automated synthesis of phosphorothioates of a different nucleotide multimers. Examples 3 and 4 describe the use of a different sulfurizing reagent of the present invention for automated synthesis of nucleotide multimers. Examples 5 and 6 are similar to Examples 1 through 4 but illustrate the use of different reagents. Example 7 describes the use of a further sulfurizing agent of the present invention for automated synthesis of various phosphorothioate nucleotide multimers, while Example 8 is similar to Example 7 but describes the use of different reagents. Examples 9 through 11 also describe the use of sulfurizing reagents of the present invention in the automated synthesis of various nucleotide multimers. Example 12 illustrates the Tm (melting temperature) of hybrids formed by the hybridization of phosphorothioate analogs with a complementary RNA sequence.

EXAMPLE 1

Automated Synthesis of Phosphorothioate Analog of TTTT.

FIG. 3 illustrates the scheme for the synthesis of the phosphorothioate analog of TTTT.

Materials: Gold label elemental sulfur, carbon disulfide and diisopropylethylamine ("DIEA") were purchased from Aldrich Fine Chemicals, Milwaukee, Wis. Nucleoside phosphoramidites, 15-umol T-column, Tetrazole and Cap B (10% dimethylamino pyridine (DMAP) in tetrahydrofuran (THF) were purchased from Biosearch, Inc., San Rafael, Calif. Cap A (10% acetic anhydride (AC$_2$O) in THF) was prepared from distilled acetic anhydride (Aldrich). 2.5% trichloroacetic acid in dichloromethane was prepared from gold label trichloroacetic acid (Aldrich). Acetonitrile, dichloromethane and tetrahydrofuran, all containing less than 0.002% water were purchased from J. T. Baker.

The scheme of FIG. 3 outlines the steps involved in the automated synthesis of a nucleotide tetramer involving automated sulfurization of the phosphite intermediate 19. Synthesis was performed on Biosearch 8750 DNA synthesizer using a modified version of the standard synthesis cycle. This modification makes use of an aqueous wash (10% water in 2% pyridine-THF) step prior to the oxidation step. This modification was included to minimize side reactions in the overall synthesis. Sulfurization was achieved by delivering a 0.2 molar solution of elemental sulfur in 50% carbon disulfide/ 50% diisopropylethylamine, (all percentages by volume unless otherwise indicated) for 15 seconds and letting it stand in the 15 μmol T-column for 30 seconds. After the sulfurization, the column and the delivery lines were washed with acetonitrile before beginning the next cycle of addition of the next base of the sequence.

As shown in FIG. 3, the synthetic procedure is initiated using 5'-O-dimethoxytrityl-thymidine linked to controlled pore glass (CPG), reagent 16. as described, for example, in U.S. Pat. No. 4,458,066. The 5'-dimethoxytrityl (DMT) protecting group is removed using acid catalysis to form the deprotected intermediate 17 which is coupled to the thymidine phosphoramidite 18 to form dimer 19. Any unreacted 17 is capped by treatment with acetic anhydride and dimethylaminopyridine. The dimer 19 is sulfurized with the same sulfurization reagent consisting of 0.2 M sulfur in 50% $CS_2$/50% DIEA to form the phosphorothioate triester 20. The 5'-protecting group is then removed as before to form dimer 21 and the trimer (not shown) assembled using the thymidine phosphoramidite 18 which is then sulfurized and deprotected, followed by assembly of a tetramer using thymidine phosphoramidite 18. Sulfurization of the tetramer and removal of the 5'-protecting group in the same manner as described, provides tetramer 22.

After tetramer 22 had been assembled, the resin from the column was transferred into a screw-cap tube and heated with concentrated ammonium hydroxide at 55° for 8-10 hours to form 23. Ammonium hydroxide was then evaporated off to give 300 OD units of the product. An analytical examination of the purity was performed by gel electrophoresis of 2 OD units of the crude product on a 10% acrylamide gel containing 7 M urea. The product was largely one band (ca 95%) as shown by UV shadowing.

The extent to which the "sulfur" had been added to the "phosphorus" of the phosphite intermediate was determined by $^{31}P$ nuclear magnetic resonance (NMR) in $D_2O$. Absence of $^{31}P$ resonance at $-2.688$ PPM in the NMR spectrum of the phosphorothioate analog of T-T-T-T ($^{31}P$, 53.866 PPM) indicates that the extent of sulfurization is almost quantitative.

EXAMPLE 2

The use of the sulfurization reagent was then extended to the synthesis of a phosphorothioate analog of a longer nucleotide multimer. This longer multimer was synthesized and deblocked the same way as described in Example 1 but purified by gel electrophoresis (20% acrylamide—7M urea). The product was visualized though UV shadowing, the slow moving band was sliced off and extracted with 0.1 M ammonium acetate (pH 7.2) and desalted on sep-pak followed by a second desalting on Pharmacia's Nap-25 column. Such a desalted multimer was labeled with δ-$ATP^{32}$ and gel electrophoresed to check the analytical purity. The following phosphorothioate multimer was synthesized (the designation "PS" before the 5' end of the multimer sequence indicating the phophorous of all nucleotide linking groups has been sulfurized):

a  PS-GCTCGTTGCGGGACTTAACCCAACAT  ("26-mer").

The phosphorothioate analog of the multimer moved very closely in gel electrophoresis to the corresponding normal multimer.

EXAMPLE 3

The procedure of Example 1 was repeated except using as a sulfurization reagent, 0.2 M sulfur in 50% $CS_2$/50% triethylamine ("TEA") (Gold label; Aldrich), to successfully produce PS-TTTT.

EXAMPLE 4

The procedure of Example 2 was repeated except using as a sulfurization reagent 0.2 M sulfur in 50% $CS_2$/50% TEA. In both this Example and in Example 3, the respective sulfurized nucleotide multimers were obtained. However, the sulfurization reagent of Examples 1 and 2 is preferred over that of this Example and Example 3, since it was found that when TEA was used as the tertiary amine rather than DIEA, a brown glue like substance started appearing in the flask after about 6 hours, which was not the case when DIEA was used (the S/$CS_2$/DIEA showing no signs of instability even after 3 days).

EXAMPLE 5

The procedure of Examples 1 and 2 were repeated to again successfully produce PS-TTTT, and a (the 26-mer), but using the methoxy, rather than the β-cyanoethoxy, phosphoramidites of the nucleosides of the formula:

ipr = isopropyl
DMT = dimethoxytrityl (4,4'-dimethoxytriphenylmethyl).

EXAMPLE 6

The procedures of Examples 3 and 4 were repeated to again successfully produce the PS-TTTT and a (the 26 mer), but using the methoxy phosphoramidites of Example 5.

EXAMPLE 7

A sulfurization reagent was prepared consisting of 0.2 M S in 25% $CS_2$/25% pyridine/50% TEA. The procedure of Example 1 was the repeated except using the foregoing sulfurization reagent. The procedure of Example 2 was also repeated, to prepare (the 26-mer), using the foregoing sulfurization reagent. In addition, using the foregoing sulfurization reagent and the procedure of Example 2, the following nucleotide multimers were also successfully prepared:

| | | |
|---|---|---|
| b | PS-TTAACCCAACAT | (12-mer) |
| c | PS-GACTTAACCCAACTAT | (15-mer) |
| d | PS-GCTCGTTGCGGGACTTAACCC | (21-mer). |

EXAMPLE 8

The procedure of Example 7 was repeated, but successfully prepare the sulfurized oligomers a, b, c, and d.

EXAMPLE 9

The procedure of Example 1 was again essentially repeated except using the methyl, rather than the β-cyanoethoxy, phosphonamidite of the T-nucleoside having the formula:

ipr = isopropyl.

In addition, the sulfurization reagent used was 0.2 M sulfur in 25% CS₂/25% pyridine/50% TEA. Further, in order to cleave the PS-nucleotide from the resin, the resin was treated at room temperature with 1 ml of a 1:1 (by volume) mixture of ethylenediamine/EtOH for 6 hours.

The resulting product was PS-TTTT in which the nucleosides are linked by methyl phosphonodiester groups.

EXAMPLE 10

The procedure of Example 2 was essentially repeated to prepare the sulfurized 15-mer of c, except using the methyl phosphonamidite and the cleavage procedure Example 9. The resulting oligomer has the sequence c in which the nucleosides are linked by methyl phosphonothioate diester groups.

EXAMPLE 11

Example 9 was repeated except the sulfurizing reagent used as 0.2 M sulfur in 50% CS₂/50% DIEA (which as previously mentioned is preferred over that using TEA, or that in which pyridine is additionally present). The resulting product was again the PS-TTTT oligomer in which the nucleotides are linked by methyl phosphonothioate diester groups of the formula:

EXAMPLE 12

The table below compares the Tm of two phosphorothioate analogs with normal nucleotide multimers. The P³² labeled nucleotide multimer was hybridized with *E. coli* RNA in 0.48 M phosphate buffer, the hybrid bound to hydroxyapatite resin and the thermal stability measured in 0.1 M phosphate buffer:

|  | Tm °C. | |
| --- | --- | --- |
|  | Normal Multimer | Phosphorothioate Multimer |
| 15-mer | 41.8 | 40.3 |
| 26-mer | 66.1 | 50.9 |

The foregoing Examples illustrate specific applications of the invention. Other useful applications of the invention which may be a departure from the specific Examples will be apparent to those skilled in the art. Accordingly, the present invention is not limited to those examples described above.

I claim:

1. A method of sulfurizing an organic compound selected from a nucleoside phosphite and a nucleoside phosphonite, wherein said organic compound comprises a trivalent phosphorus able to be sulfurized, to produce a nucleotide multimer with at least two nucleosides linked together to form a phosphorothioate or phosphonothioate group, said method comprising the steps of: providing a nucleoside phosphite or nucleoside phosphonite attached to a solid-phase support, contacting said nucleoside phosphite or nucleoside phosphonite with a solution of sulfur, a non-aromatic tertiary amine sized to allow the sulfurization, and a solvent able to solubilize sulfur so as to sulfurize the internucleotide phosphite or phosphonite to produce the corresponding internucleotide phosphorothioate or phosphonothioate group, wherein the sulfurization occurs on a nucleotide multimer synthesizer, and wherein the sulfurization occurs within about 45 seconds without heating.

2. A method as defined in claim 1 wherein the first nucleoside phosphite or nucleoside phosphonite is selected from a dinucleoside phosphite triester and a dinucleoside organophosphonite diester.

3. A method as defined in claim 1 wherein the tertiary amine is a trialkyl amine.

4. A method as defined in claim 1 wherein the solvent is an organic solvent.

5. A method as defined in claim 1 wherein the solvent is carbon disulfide.

6. A method as defined in claim 2 or 1 wherein the solvent comprises carbon disulfide.

7. A method as defined in claim 2 or 1 wherein the solvent is an organic solvent and the tertiary amine is a trialkyl amine.

8. A method as defined in claim 2 or 1 wherein the solvent comprises carbon disulfide, the tertiary amine is a trialkyl amine.

9. A method as defined in claim 1 wherein the solution of sulfur and a trialkyl amine in the organic solvent has substantially equal parts by weight of the trialkyl amine and the organic solvent, and has a sulfur concentration of at least about 0.2 M.

10. A method as defined in claim 9 wherein the organic solvent is carbon disulfide and the trialkyl amine is selected from triethylamine and diisopropylethylamine.

11. The method of claim 1 wherein the organic compound is selected from compounds of the formula:

wherein R₁ and R₂ are nucleosides and R₃ is selected from the group consisting of an alkyl group and a leaving group which can be selectively cleaved following sulfurization, and wherein said R₁, R₂ and R₃ allow sulfurization of said phosphorus, to form a corresponding organic phosphorus thioester of the formula:

12. A method as defined in claim 11 wherein the tertiary amine is a trialkyl amine.

13. A method as defined in claim 12 wherein the solvent comprises carbon disulfide.

14. A method as defined in claim 13 wherein the tertiary amine is selected from triethyl and diisopropylethylamine.

15. A method as defined in claim 14 wherein the sulfur concentration is at least about 0.2 M.

16. A method as defined in claim 15 wherein the solution of sulfur and the trialkyl amine comprises substantially equal parts by weight of the trialkyl amine and the organic solvent.

17. A method as defined in claim 11, 12, or 16, wherein $R_3$ is selected from an optionally substituted alkyl, alkoxy, phenoxy, and tertiary amino, or analogues thereof.

18. A method as defined in claim 11, 12, or 16 wherein $R_3$ is selected from methyl, methoxy, and $\beta$-cyanoethoxy.

19. A method as defined in claim 11, 12, or 16 additionally comprising cleaving the leaving group following sulfurization.

20. A method as defined in claim 1 wherein the tertiary amine is diisopropylethylamine.

21. A method as defined in claim 1 wherein the nonaromatic tertiary amine is diisopropylethylamine and the solvent is carbon disulfide.

22. A method as defined in claim 1 or 21 wherein the solid phase support is controlled pore glass.

* * * * *

UNITED STATES PATENT AND TRADEMARK OFFICE
CERTIFICATE OF CORRECTION

PATENT NO. : 5,252,723
DATED : October 12, 1993
INVENTOR(S) : Ram S. Bhatt

It is certified that error appears in the above-indentified patent and that said Letters Patent is hereby corrected as shown below:

Column 4, Line 1: of the kind <u>12</u> (see . . . .

column 4, Line 38: of a nucleic <u>acid.</u>

Column 5, Line 51: Pat. No. 4,[7]<u>6</u>25,677 and . . .

Column 7, Line 1: reagent 16 [.]<u>,</u> as . . . .

Column 8, Line 46: prepare <u>a</u> (the . . .

column 8, Line 60: repeated, but <u>using the methoxy phosphoramidites of the nucleotides, to successfully</u> . . .

Signed and Sealed this

Twentieth Day of September, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,252,723
DATED      : October 12, 1993
INVENTOR(S) : Ram S. Bhatt

It is certified that error appears in the above-indentified patent and that said Letters Patent is hereby corrected as shown below:

On the title page item [73], should read --Gen-Probe Incorporated--.

Signed and Sealed this

Twentieth Day of December, 1994

Attest:

BRUCE LEHMAN

*Attesting Officer*  *Commissioner of Patents and Trademarks*